(12) United States Patent
Comings et al.

(10) Patent No.: US 6,869,768 B2
(45) Date of Patent: Mar. 22, 2005

(54) ASSOCIATION BETWEEN THE ACID PHOSPHATASE (ACP1) GENE AND ALZHEIMER'S DISEASE

(75) Inventors: David E. Comings, Duarte, CA (US); James P. MacMurray, Loma Linda, CA (US)

(73) Assignee: City of Hope, Duarte, CA (US)

( * ) Notice: Subject to any disclaimer, the term of this patent is extended or adjusted under 35 U.S.C. 154(b) by 323 days.

(21) Appl. No.: 10/236,916

(22) Filed: Sep. 9, 2002

(65) Prior Publication Data

US 2003/0110523 A1 Jun. 12, 2003

Related U.S. Application Data

(60) Provisional application No. 60/317,475, filed on Sep. 7, 2001.

(51) Int. Cl.[7] .................................................. C12Q 1/68
(52) U.S. Cl. .......................................... 435/6; 435/91.2
(58) Field of Search ..................... 435/6, 91.2; 536/23.1

(56) References Cited

PUBLICATIONS

Spencer et al. Quantitative Differences and Gene Dosage in the Human Red Cell Acid Phosphatase Polymorphism, Nature, Jan. 18, 1964, p. 299–300.*

Sensabaugh et al. A TaqI site identifies the *A allele at the ACP1 locus. Human Molecular Genetics, 1993, vol. 2, No. 7, p. 1079.*

Alzeheimer's Disease Collaborative Group, "The structure of the presenilin 1 (S182) gene and identification of six novel mutations in early onset AD families," Nature Genet., 11:219–222, 1995.

Arai, H. et al., "CSF phosphorylated tau protein and mild cognitive impairment: a prospective study," Exp Neurol, 166:201–3, 2000.

Bryson, G. L. et al., "Gene structure, sequence, and chromosomal localization of the human red cell–type low–molecular–weight acid phosphotyrosyl phosphatase gene, ACP1," Genomics, 30:133–40, 1995.

Comings, D. E. et al., "The additive effect of neurotransmitter genes in pathological gambling," Clinical Genetics, 60:107–116, 2001.

Comings, D. E. et al., "Why different rules are required for polygenic inheritance: Lessons from studies of the DRD2 Gene," Alcohol, 16:61–70, 1998.

Comings et al., "A multivariate analysis of 59 candidate genes in personality traits: the temperament and character inventory," Clin Genet 58:375–385, 2000.

Comings et al., "Polygenic inheritance and micro/minisatellites," Mol Psychiatry 3:21–31, 1998.

Comings et al., "Multivariate analysis of associations of 42 genes in ADHD, ODD and conduct disorder," Clin Genet 58:31–40, 2000.

Comings, D. E., "Molecular heterosis as the explanation for the controversy about the effect of the *DRD2* gene on dopamine $D_2$ receptor density," Scientific Correspondence, 213–215, May 1999.

Daly, N. L. et al., "Role of phosphorylation in the conformation of tau peptides implicated in Alzheimer's disease," Biochemistry, 39:(30) 9039–46, 2000.

Grant, W. B., "Dietary links to Alzheimer's disease," Alzheimer's Disease Review 2: 42–55, 1997.

Iijima, K. et al., "Neuron–specific phosphorylation of Alzheimer's beta–amyloid precursor protein by cyclin–dependent kinase 5," J Neurochem, 75:(3), 1085–91, 2000.

Ikura, Y. et al., "Levels of tau phosphorylation at different sites in Alzheimer's disease brain," NeuroReport, 9:2375–2379, 1998.

Iqbal, K. et al., "Mechanisms of neurofibrillary degeneration and the formation of neurofibrillary tangles," J Neural Transm, Suppl. 53: 169–80, 1998.

Iqbal, K. et al., "Defective brain microtubule assembly in Alzheimer's disease," The Lancet, 421–426, 1986.

Karlinsky, H. et al., "Molecular and prospective phenotypic characterization of a pedigree with familial alzheimer's disease and a missence mutation in codon 717 of the β–amyloid precursor protein gene," Neurology, 42: 1445–1453, 1992.

Kehoe, P. et al., "A full genome scan for late onset Alzheimer's disease," Hum Mol Genetics, 8:(2) 237–45, 1999.

Kimura, T. et al., "Phosphorylation of MARCKS in alzheimer disease brains," NeuroReport, 11(4), 869–73, 2000.

Lovestone, S. et al., "Alzheimer's disease–like phosphorylation of the microtubule–associated protein tau by glycogen synthase kinase–3 in transfected mammalian cells," Current Biology, 4:(12) 1077–1086, 1994.

Morris, J. C. et al., "Mild cognitive impairment represents early–stage Alzheimer disease," Arch Neurol, 58:397–405, 2001.

(List continued on next page.)

Primary Examiner—Juliet C. Switzer
(74) Attorney, Agent, or Firm—Rothwell Figgs Ernst & Manbeck (57) ABSTRACT

Alzheimer's disease is characterized by the presence of senile plaques formed from beta amyloid (Aβ), and neurofibrillary tangles (NTFs) formed from paired helical filaments consisting of hyperphosphorylated tau. A number of studies have shown that the NTFs correlate better with the duration and severity of Alzheimer's disease than senile plaques. However, a criticism of the primary etiological role of NTFs in Alzheimer's disease is the absence of variants of kinases or phosphatases associated with Alzheimer's disease. Acid phosphatase, a product of the ACP 1 gene, is a ubiquitous low molecular weight protein tyrosine phosphatase. A common allele, ACP 1*A, is associated with a lower activity of acid phosphatase. It is due to an Arg 105 Gln substitution of the ACP1 locus and detected as a Taq I polymorphism. We report a significant association of the low activity 2 allele with sporadic early onset Alzheimer's disease (EOAD). These findings support the possibility that other variants of kinase and genes may be associated with sporadic Alzheimer's disease.

3 Claims, 1 Drawing Sheet

OTHER PUBLICATIONS

Omar, R. et al., "Acid phosphatase activity in senile plaques and cerebrospinal fluid of patients with Alzheimer's disease," *Arch Pathol Lab Med.,* 117:166–9, 1993.

Russ, C. et al., "Identification of sequence variants and analysis of the role of glycogen synthase kinase 3 β gene and promoter in late onset Alzheimer's disease," *Mol. Psychiatry,* 6: 320–324, 2001.

St George–Hyslop et al., "The genetic defect causing familial Alzheimer's disease maps on chromosome 21," *Science,* 235:885–890, 1987.

Schellenberg, G. D. et al., "Genetic linkage evidence for a familial Alzheimer's disease locus on chromosome 14," *Science,* 258:668–671, 1992.

Selkoe, D.J. "Toward a comprehensive theory for Alzheimer's disease. Hypothesis: Alzheimer's disease is casued by the cerebral accumulation and cytotoxicity of amyoid b–protein," *Ann. N.Y Academy Sciences,* 924: 17–25, 2000.

Sensabaugh, G. F. et al., "A Taql site identifies the *A allele at the ACP1 locus," *Hum. Mol. Genetics,* 2:(7)1079, 1993.

Shimohama, S. et al., Alterations of low molecular weight acid phosphatase protein level in Alzheimer's disease. *Brain Res,* 699: 125–9, 1995.

Shimohama, S. et al., "Reduction of low–molecular–weight acid phosphatase activity in Alzheimer brains," *Ann. Neurol. Assoc.,* 33:616–21, 1993.

Shirazi, S. K. et al., "The protein tyrosine kinase, fyn, in Alzheimer's disease pathology," *NeuroReport,* 4:(4)435–7, 1993.

Standen, C. L. et al., "Phosphorylation of thr($^{668}$) in the cytoplasmic domain of the Alzheimer's disease amyloid precursor protein by stress–activated protein kinase 1b (Jun N–terminal kinase–3)," *Journal of Neurochem,* 76:316–20, 2001.

Su, J. H. et al., "Early phosphorylation of tau Alzheimer's disease occurs at Ser–202 and is preferentially located within neurites," *NeuroReport,* 5(17):2358–2362, 1994.

Tanino, H. et al., "Abundance of low molecular weight phosphotyrosine protein phosphatase in the nerve–ending fraction in the brain," *Biol Pharm Bull,* 22(8):794–8, 1999.

Vogelsberg–Ragaglia, V. et al., "PP2A mRNA Expression Is Quantitatively Decreased in Alzheimer's Disease Hippocampus," *Exp Neurol,* 168:402–12, 2001.

Walter, J. et al., Phosphorylation of the beta–amyloid precursor protein at the cell surface by ecotcasein kinases 1 and 2*, *The Journal of Biological Chemistry,* 275:(31)23523–9, 2000.

Yin–Zhang, Z et al., "Purification and Characterization of a Low–Molecular–Weight Acid Phosphatase—A Phosphotyrosyl–Protein Phosphatase from Bovin Heart," *Archives of Biochemistry and Biophysics,* 282(1):39–49, 1990.

* cited by examiner

Figure 1

SEQUENCE LISTING

```
<160> NUMBER OF SEQ ID NOS: 2
<210> SEQ ID NO 1
<211> LENGTH: 21
<212> TYPE: DNA
<213> ORGANISM: Artificial Sequence
<220> FEATURE:
<223> OTHER INFORMATION: PCR primer for ACP1 polymorphic region

<400> SEQUENCE: 1
ttcagaagac cctagcagat g                                              21

<210> SEQ ID NO 2
<211> LENGTH: 26
<212> TYPE: DNA
<213> ORGANISM: Artificial Sequence
<220> FEATURE:
<223> OTHER INFORMATION: PCR primer for ACP1 polymorphic region

<400> SEQUENCE: 2
acataatagg gatcttcgat aataag                                         26
```

ASSOCIATION BETWEEN THE ACID PHOSPHATASE (ACP1) GENE AND ALZHEIMER'S DISEASE

CROSS-REFERENCE TO RELATED APPLICATION

The present application is related to and claims priority under 35 U.S.C. § 119(e) to U.S. provisional patent application Ser. No. 60/317,475, filed Sep. 7, 2001.

FIELD OF THE INVENTION

This invention relates generally to the field of human genetics. More specifically, the invention relates to human germline mutations or polymorphisms in the ACP1 gene, methods and materials used to isolate and detect said mutations or polymorphisms and further to their use in diagnosis of Alzheimer's disease and screening drug candidates for treatment of Alzheimer's disease.

The publications and other materials used herein to illuminate the background of the invention or provide additional details respecting the practice are incorporated by reference and for ease of reference are included in the Bibliography.

BACKGROUND AND SIGNIFICANCE

Alzheimer's disease is the most common cause of dementia and affects roughly four million individuals. The ultimate goal of understanding the causes of Alzheimer's disease is to identify better methods of treatment and prevention. About 5 to 12% of Alzheimer's disease is due to autosomal dominant genes. The genes involved include the AD1 locus for the APP gene on chromosome 21 (St George-Hyslop et al. 1987) that codes for the Amyloid Precursor Protein (APP) (Karlinsky et al. 1992) and contains the sequences of amyloid-β (Aβ) present in senile plaques, the AD3 locus for PS-1 gene on chromosome 14 (Schellenberg et al. 1992; Alzheimer's Disease Collaborative Group 1995; Sherrington et al.1995; Sandbrink et al.1996) and the AD4 locus for PS-2 on chromosome 1 (Levy-Lahad et al.1995; Rogaev et al.1995).

The majority of Alzheimer's disease cases are sporadic. The AD2 locus for the APOE gene on chromosome 19 is an important locus for sporadic Alzheimer's disease (Saunders et al.1993; Saunders et al. 1996). The three major alleles are e2, e3 and e4, differing in two residues at position 112 and 158. The e4 allele is associated with an increased risk for Alzheimer's disease. It is present in 14% of normal Caucasians versus 37% in sporadic late-onset Alzheimer's disease (LOAD), and 48% in LOAD subjects with a family history of Alzheimer's disease (Saunders et al. 1993; Poirier et al.1993; Strittmatter et al. 1993). PS-1 has also been suggested as a risk factor for some cases of LOAD.

Based on studies of a number of different countries, factors such as dietary fat and total caloric intake have been shown to be highly correlated with the prevalence of Alzheimer's disease (Grant 1997). While this might seem to imply that environmental factors are more important than genetic ones, it is more likely that this represents the results of genetic environmental interaction. For example, a high fat diet may produce oxidative stress, and individuals genetically susceptible to such stress may be the ones who develop Alzheimer's disease. In the absence of a high fat diet the oxidative stress is too small to produce Alzheimer's disease even in genetically susceptible individuals.

Tau hyperphosphorylation. The presence of paired helical filaments (PHF) forming neurofibrillary tangles (NFTs) is one of the diagnostic characteristics of Alzheimer's disease (Iqbal et al.1986). NFTs are composed of an insoluble complex of microtubule (MT) proteins and hyperphosphorylated MT associated protein, tau. The degree of tau phosphorylation has been shown to correlate well with the degree of dementia (Iqbal et al.1986) and with the degree of minimal cognitive defect (MCI), a precursor to Alzheimer's disease (Arai et al.2000; Morris et al. 2001). Tau is moderately hyperphosphorylated in MCI and phosphorylated to an even greater degree in Alzheimer's disease (Su et al.1994; Ikura et al. 1998; Mailliot et al.1998; Spencer et al. 1964). Normally phosphorylated tau binds to tubulin and contributes to the assembly and stabilization of MT (Tseng et al. 1999). Hyperphosphorylated tau loses its ability to bind to tubulin, self-aggregates and contributes to the formation of PHF and NFTs (Iqbal et al.1986; Iqbal et al.1998).

APP phosphorylation. Okadaic acid (OA), is an inhibitor of protein phosphatases PP1 and PP2A. This compound has played an important role in the demonstration of the important role of phosphorylation of APP and other amyloid products in Alzheimer's disease. Holzer et al. (2000) examined the effect of OA on primary cultures of guinea pig neurons. Since guinea pig APP is 98% homologous to human APP at the protein level, identical regarding the Aβ sequence and is processed in a similar manner as human APP, this serves as a good animal model. Both intracellular and secreted APP was upregulated by OA treatment of 14 days old cultures in a concentration dependent manner.

Threonine(668) is within the carboxy-terminus of the Alzheimer's disease amyloid precursor protein (APP) and is a known in vivo phosphorylation site. Phosphorylation of APPthr(668) has been proposed to play a role in the regulation of APP function, metabolism and location (Iijima et al. 2000). APP is one of the rare proteins known to be phosphorylated within its ectodomain (Walter et al. 2000). Since Thr(688) is next to a proline, Standen et al. (2001) examined the potential role of proline-directed kinases in thr(688) phosphorylation. They found that stress-activated protein kinase-1b (SAPK1b) induced a robust phosphorylation of this site both in vitro and in vivo. They suggested that this finding provided a molecular framework to link cellular stresses with APP metabolism. Walter et al. (2000) have shown that membrane-bound beta APP as well as secreted forms of betaAPP can be phosphorylated by casein kinase (CK) 1- and CK2-like ectoprotein kinases.

Activation of the amyloid beta-protein precursor secretary pathway through alpha-secretase has been reported to increase the secretion of neuroprotective amyloid precursor protein and preclude the formation of amyloid beta-protein. Activation of protein kinase C has been shown to accelerate this secretory pathway (McLaughlin et al.1999). Thus, low levels of PKC would be expected to accelerate the deposition of Aβ. Kimura et al. (2000) showed that the levels of PKC were lower in Alzheimer's disease compared to control brains. Tan et al. (1997) has suggested that phosphorylation of Aβ plays a role in regulating its toxicity.

This is just a sampling of the many reports that suggest that in addition to the role of phosphorylation of tau in Alzheimer's disease, the phosphorylation of APP, Aβ and other amyloid related proteins also plays an important role in the etiology of Alzheimer's disease.

Okadaic acid and the genetics of Alzheimer's disease. Arendt et al.(1995) reported that chronic infusion into rat brain ventricles of OA resulted in a severe memory impairment, accompanied by a paired helical filament-like phosphorylation of tau protein and the formation of beta/

A4-amyloid containing plaque-like structures in gray and white matter areas. In addition to its effect on the inhibition of phosphatases, OA directly or indirectly stimulates tau and other kinases. Adendt et al. suggested that an imbalance between protein phosphorylation [kinases] and dephosphorylation [phosphatases] might be crucial for the development of the molecular hallmarks of Alzheimer's disease.

Russ et al. (2001) recently examined the potential association between the glycogen synthase kinase 3β gene (GSK3B) and late onset Alzheimer's disease. They examined two SNPs in the promoter region, A/T-1727 and T/C-40. The frequency of the minor alleles were 0.13 and 0.35 respectively. They were in strong but not complete linkage disequilibrium (d'=0.48, p=$\leq 10^{-7}$). Neither was significantly associated with late onset Alzheimer's disease (p=$\leq 0.16$ for both, odds ratios=1.3 and 1.2 respectively). They also identified three other rare SNPs with minor allele frequencies of less than 0.05. None of these were associated with Alzheimer's disease. This does not rule out a role of the GSK3B gene in Alzheimer's disease, since early Alzheimer's disease (EOAD) was not examined and combined the two common polymorphisms screened less than 60 percent of the possible haplotypes at this locus.

Tau is normally phosphorylated by the addition of phosphate groups to threonine and serine residues. The maintenance of normal levels of phosphorylation of tau is due to a balance between phosphorylation and dephosphorylation. Numerous candidate enzymes for the phosphorylation of tau have been proposed including glycogen synthase kinase 3 (Lovestone 1997), NCLK (CDK5 and p35/p25) (Hopkinson et al.1980; Sobue et al.2000; Kerokoski et al. 2001), CaMKII (Bennecib 2001), and others (Spencer et al. 1964; Tseng et al.1999; Lovestone1997; Guise S et al. 2001; Flaherty et al.2000). The kinases can be divided into proline-directed kinases and non-proline-directed kinases. Many of the serine and threonine residues are adjacent to prolines, implicating a role of proline-directed kinases. The proline directed kinases shown to play a role in tau phosphorylation include glycogen synthase kinase-3β (Lovestone 1997; Lovestone et al.1994; Sperber et al.1995), CDK5 and p35/p25 (Hopkinson et al.1980; Sobue et al.2000; Kerokoski et al. 2001; Pei et al.1998), CDC2 (Oawal et al.1992), p42 and p44 MAPK (Goedert et al.1992). The non-proline directed kinases include CaMKII (Bennecib et al. 2001), c-AMP-PK, PKC, casein kinases 1 and 2, TTK, PKN and p110$^{MARK}$ (Spencer et al.1964; Tseng et al.1999; Lovestone 1997; Guise et al.2001; Flaherty et al.2000; Taniguchi et al. 2001; Masliah et al.1990; Shapiro et al.1991).

Tau phosphatases. A number of enzymes that dephosphorylate tau have been identified (Lovestone 1997). These include the serine/threonine phosphatases PP1, PP2A, and PP2B (calcineurin). Sontag et al. (1996;1999) identified an important role of protein phosphatase 2A (PP2A) in the dephosphorylation of tau. The expression of PP2A is decreased in the hippocampus in Alzheimer's disease (Vogelsberg-Ragaglia et al. 2001). The catalytic unit of PP2A dephosphorylates tau serine 396 but not 199 and 202, while the holoenzyme dephosphorylates all three (Ono et al.1995). This was also the case for PP2B.

An additional candidate is acid phosphatase 1 (ACP1), a ubiquitous enzyme present in all tissues including the brain (Tanino et al.1999). ACP1 is also known as low molecular weight protein tyrosine phosphatase (LMWPTP). It shows no significant serine or threonine phosphatase activity (Zhang et al.1990; Chernoff et al. 1985) and thus is unlikely to be directly involved in tau phosphorylation. However, biochemical analysis and studies with specific antibodies to LMWPTP show that the level of ACP1 protein is significantly decreased in Alzheimer's disease brains (Shimohama et al. 1995; Shimohama et al.1993). ACP2, a lysosomal acid phosphatase, is associated with senile plaques in Alzheimer's disease (Omar et al.1993; Suzuki et al. 1967; Kawai et al.1992), and PTPRC, a protein tyrosine phosphatase receptor type also known as CD45, has also been implicated in Alzheimer's disease (Masliah et al. 1991).

The ACP1 gene spans 18 kb, 157 amino acids and consists of seven exons. Genetic variants of ACP1 have been recognized for many years. There are three major variants: ACP1*A, *B, and *C. Each of the three variants show two isoenzymes, slow and fast, due to a variant region spanning 34 nucleotides. This variant region is the result of alternate splicing such that two different exons, each 114 bp in length, are present in each isoform. ACP1*A differs from ACP1*B and *C by the presence of a Gln>Arg substitution at codon position 105 (Bryson et al.1995; Lazaruk et al.1993; Dissing et al.1992).

An A>G polymorphism of ACP1*A has been identified which creates a Taq I restriction endonuclease site in ACP1 that allows PCR based genotyping of ACP1. Restriction digestion of a 149 base pair(bp) PCR product from ACP1 with known oligonucleotide primers generated a 149 bp fragment from the intron 5' of the C2 exon and into the C2 exon (Sensabaugh et al.1993). In the ACP1*A allele, the A>G sequence contains a target site for the restriction endonuclease Taq1. Cleavage of the 149 bp product with Taq1 enzyme generated 105 and 41 bp fragments when the ACP1*A allele was the substrate and ACP1*B and ACP1*C allele products were not cut with this enzyme(Id.).

Since ACP1*A has a lower enzyme activity than APC1*B or *C (Spencer et al.1964), there is a progressive decrease in ACP1 enzyme activity progressing from Taq I genotypes 11 (absence of *A variant) to 12 (50% *A variant) to 22 (100% *A variant). Thus, the term "2 allele" as used herein is meant to represent "ACP1*A" or "ACP1*A allele."

Hyperphosphorylation of both tau and Aβ are proposed to be involved in the etiology of Alzheimer's disease. ACP1 is widely distributed in the brain and has been shown to be present in low levels in Alzheimer's disease brains. Polymorphisms of ACP1 are known to be associated with variations in enzyme activity, suggesting the possibility of an association of the ACP1*A allele of the ACP1 Taq I polymorphism with Alzheimer's disease.

Although NFT and senile plaques are characteristic of Alzheimer's disease, it has generally been thought that the Aβ cascade is most likely to be causative of Alzheimer's disease. It is consistent with many of the observations about the pathophysiology of Alzheimer's disease (Selkoe et al.2000). Despite this, a number of reports have shown that NFT rather than senile plaques more closely parallel both the duration and the severity of Alzheimer's disease (Arriagada et al.1992; Terry et al.1994; Braak et al.1996). One of the criticisms of a primary role of hyperphosphorylated tau in Alzheimer's disease has been the lack of evidence for a specific defective kinase or phosphatase in Alzheimer's disease (Daly et al. 2000).

Shirazi and Wood identified a subset of neurons in Alzheimer's disease brain that exhibited intense fyn tyrosine kinase immunoreactivity (Shirazi and Wood 1993). Double label immunohistochemistry showed that these fyn-positive neurons were also positive for hyperphosphorylated tau. They proposed that the activity of proline-directed tau kinases were regulated by fyn. APC1 may play an indirect role in the regulation of tau phosphorylation by counteracting the activity of fyn-kinase. Under this hypothesis low levels of ACP1 activity could play a role in the intense fyn immunostaining observed in some parts of Alzheimer's brain. Fyn is also able to directly phosphorylate tau at tyrosine residues. ACP1 could also be involved in direct dephosphorylation of such tau tyrosine residues. Studies of a synthetic portion of tau have shown that phosphorylation of a serine residue had little impact on conformation while phosphorylation of a tyrosine residue, resulted in considerable conformational change (Lee et al. 1998).

Some of the known substrates of ACP1 are the platelet derived growth factor (PDGF) and the insulin receptor (Taddei et al. 2000). ACP1 itself is phosphorylated, via Src and Src-related kinases, upon stimulation of cells with PDGF (Bucciantini et al. 1999; Cirri et al.1998). The observation of a significant association between the hypoactive variant of ACP1 is consistent with a direct or indirect role of this gene in the hyperphosphorylation of tau characteristic of NFTs or changes in the phosphorylation of APP playing a role in the production of Aβ.

While a single gene defect in a tau kinase or a tau phosphatase producing Alzheimer's disease has yet to be identified, the wide number of enzymes shown to phosphorylate and dephosphorylate tau and amyloid provide a rich substrate for an additive and epistatic effect of a series of genetic variants of the genes that regulate tau and APP phosphorylation. The present study suggests that an additive or epistatic effect of two or more genes, consisting of a combination of a hyperexpressed kinase and a hypoexpressed phosphatase could account for a sizeable proportion of the variance of Alzheimer's disease.

SUMMARY OF THE INVENTION

The present invention relates to the ACP1*A polymorphism in the ACP1 gene and use of a nucleic acid specific for this allele to detect the allele as an aid in the diagnosis and prognosis of Alzheimer's disease. The invention also relates to methods for the treatment of Alzheimer's disease associated with the ACP1*A polymorphism in the ACP1 gene. The invention also relates to the screening of drugs useful for the treatment of Alzheimer's disease.

In one embodiment, the invention provides a nucleic acid specific for the ACP1*A allele of ACP1. In another embodiment, the invention provides a method for screening for the presence of the ACP1*A allele in order to diagnose Alzheimer's disease or a predisposition to Alzheimer's disease in a patient. In one embodiment, the method of detecting the ACP1*A allele comprises detecting the Taq1 restriction enzyme site specific to the ACP1*A allele from genomic DNA, RNA or cDNA from said patient. In another embodiment, the invention provides a primer or probe specific for the ACP1*A allele. In another embodiment, the invention comprises a method of screening for the presence of the ACP1*A allele with said nucleic acid in order to diagnose Alzheimer's disease or a predisposition to Alzheimer's disease. In yet another embodiment, the invention provides a method for screening for the presence of said ACP1*A allele which comprises detecting the presence of the ACP1*polypeptide produced by said allele.

In another embodiment, the invention provides a non-human animal model for Alzheimer's disease which carries an altered ACP1 gene in its genome, wherein said altered ACP1 gene comprises at least one ACP1*A allele and said animal exhibits at least one sign or symptom of Alzheimer's disease. In one embodiment, the animal is homozygous for the ACP1*A allele. In another embodiment, the invention provides a cell line derived from one or more cells from the non-human animal. In a preferred embodiment, the animal comprises a mouse and the signs or symptoms associated with Alzheimer's disease are selected from the group consisting of neurofibrillary tangles; Alzheimer's plaques; memory loss; and decreased ability to learn or perform a task.

The invention further provides a method of screening for drug candidates useful in treating a disease associated with the ACP1*A polypeptide, wherein said method comprises administering a drug to a first animal which is homozygous for said polymorphism, wherein if said animal shows a decrease in signs or symptoms associated with said disease when compared to a second animal homozygous for said polymorphism that does not receive the drug, said drug is a drug candidate for treating said disease. In another preferred embodiment, said first and second animal are the same strain of a species. In a preferred embodiment, the disease is Alzheimer's disease. In a particularly preferred embodiment, the disease is early onset Alzheimer's disease and said signs and symptoms are selected from the group consisting of neurofibrillary tangles; Alzheimer's plaques; memory loss; and decreased ability to learn or perform a task.

The invention further provides a method of screening for drug candidates useful in treating a disease associated with the ACP1*A polypeptide, wherein said method comprises administering a drug to a first animal which is heterozygous for said polymorphism, wherein if said animal shows a decrease in signs or symptoms associated with said disease when compared to a second animal heterozygous for said polymorphism that does not receive the drug, said drug is a drug candidate for treating said disease. In a preferred embodiment, the disease is Alzheimer's disease. In another preferred embodiment, said first and second animal are the same strain of a species. In a particularly preferred embodiment, the disease is early onset Alzheimer's disease and said signs and symptoms are selected from the group consisting of neurofibrillary tangles; Alzheimer's plaques; memory loss; and decreased ability to learn or perform a task.

In another preferred embodiment, the invention provides tissue culture cells wherein said cells comprise a genome with at least one ACP1 allele having an ACP1*A allele.

In another embodiment, the invention provides a method of screening for drug candidates useful in treating Alzheimer's disease associated with the ACP1*A allele, wherein said method comprises the steps of: (a) growing a culture of cells which are homozygous for said allele in the presence of a drug; (b) growing a culture of cells which do not contain said allele, and (c) growing a culture of cells as which are homozygous for said allele in the absence of said drug, wherein if the cells in step (a) exhibit signs and symptoms of cell growth more like the cells in step (b) than like the cells in step (c), then said drug is a drug candidate for treating Alzheimer's disease. In a preferred embodiment, said Alzheimer's disease is early onset Alzheimer's disease. In another preferred embodiment, the signs and symptoms of cell growth observed in said method of screening are selected from the group consisting of hyperphosphorylation of tau, APP, platelet derived growth factor and insulin receptor.

In another embodiment, the invention provides a method of screening for drug candidates useful in treating Alzheimer's disease associated with the ACP1*A allele, wherein said method comprises the steps of: (a) growing a culture of cells which are heterozygous for said allele in the presence of a drug; (b) growing a culture of cells which do not contain said allele, and (c) growing a culture of cells which are heterozygous for said allele in the absence of said drug, wherein if the cells in step (a) exhibit signs and symptoms of cell growth more like the cells in step (b) than like the cells in step (c) then said drug is a drug candidate for treating Alzheimer's disease. In a preferred embodiment, said Alzheimer's disease is early onset Alzheimer's disease. In another preferred embodiment, the signs and symptoms of cell growth observed in said method of screening are selected from the group consisting of hyperphosphorylation of tau, APP, platelet derived growth factor and insulin receptor.

In another embodiment, the invention comprises method of screening for a compound which is a candidate for treating a person with Alzheimer's disease, wherein said person's genome comprises an ACP1*A allele, the method comprising (a) mixing ACP1*A and a phosphorylated substrate for ACP1*A; (b) measuring phosphatase activity of ACP1*A in step (a); (c) mixing ACP1*A, a phosphorylated substrate for ACP1*A and a compound; (d) measuring phosphatase activity of ACP1*A in step (c); and (e) comparing phosphatase activity measured in step (b) with phosphatase activity measured in step (d); wherein a compound which results in the phosphatase activity measured in step (d) being greater than the phosphatase activity measured in step (b) is a candidate for treating said person. In another preferred embodiment, the phosphorylated substrate is selected from the group consisting of tau, APP, platelet derived growth factor and insulin receptor.

In another embodiment, the invention provides a method of treating a person with Alzheimer's disease, wherein said person's genome comprises an ACP1*A allele, by administering an effective amount of an acid phosphatase to said person.

DETAILED DESCRIPTION OF THE INVENTION

The present invention provides diagnostic and prognostic methods for detecting the ACP1*A allele at the ACP1 locus. In addition, diagnostic and prognostic methods for detecting a predisposition to Alzheimer's disease can be performed by detecting alterations at the ACP1 locus, or confirming the lack of a predisposition by detecting the absence of the ACP1*A allele at the ACP1 locus. Methods of treating Alzheimer's disease are also provided.

More specifically, a method for determining whether a person is at increased risk for developing Alzheimer's disease is provided by the present invention. In accordance with this method, the ACP1 genotype of an individual is determined. The presence of the ACP1*A allele indicates an increased risk for developing Alzheimer's disease, especially early onset Alzheimer's disease.

In one embodiment, the method comprises a determination of the ACP1genotype using a probe or primer specific for an ACP1 allele at codon position 105. In a preferred embodiment, the method involves a determination of the ACP1*A genotype using a probe or primer specific for the ACP1*A allele. In another preferred embodiment, the ACP1*A allele can be detected by performing a nested PCR of the ACP1gene or a portion thereof comprising codon 105, using techniques well known in the art or described herein, followed by enzymatic digestion with TaqI to detect the ACP1*A specific polymorphic sequence.

Useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), nested PCR followed by restriction enzyme digestion, dot blot analysis and PCR-SSCP. Also useful are techniques employing DNA microchip technology.

Predisposition to Alzheimer's disease can be ascertained by testing any tissue of a human for mutations of the ACP1 gene. The presence of an ACP1*A allele can be determined by testing DNA from any tissue of the person's body. Most simply, blood can be drawn and DNA extracted from the cells of the blood. In addition, prenatal diagnosis can be accomplished by testing fetal cells, placental cells or amniotic cells for polymorphisms of the ACP1 gene.

There are several methods well known to persons of ordinary skill in the art that can be used to detect DNA sequence variation, including direct DNA sequencing, clamped denaturing gel electrophoresis, heteroduplex analysis and chemical mismatch cleavage. An allele-specific detection approach such as allele-specific oligonucleotide (ASO) hybridization can be utilized to rapidly screen large numbers of other samples for the ACP1*A mutation.

Detection of point mutations can be accomplished by molecular cloning of the allele(s) and sequencing the allele (s) using techniques well known to persons of ordinary skill in the art. Alternatively, the gene sequences can be amplified directly from a genomic DNA preparation using known techniques. The DNA sequence of the amplified sequences then can be determined directly or with restriction enzyme analysis to detect polymorphic sites such as with Taq1 and ACP1*A.

DNA sequences of the ACP1 gene which have been amplified by use of PCR may also be screened using ACP1*A allele-specific oligomer probes, each of which contains a region of the gene sequence harboring a known mutation. For example, one oligomer may be about 30 nucleotides in length (although shorter and longer oligomers can be used, as recognized by those of ordinary skill in the art), corresponding to a portion of the gene sequence. By use of a battery of such allele-specific probes, PCR amplification products can be screened to identify the presence in an individual of a ACP1*A gene mutation. Hybridization of allele-specific probes with nucleic acids amplified from cells can be performed, for example, on a nylon filter. Hybridization to a particular probe under high stringency hybridization conditions indicates the presence of the same mutation in the cells as in the allele-specific probe.

Nucleic acid analysis via microchip technology is also applicable to the present invention. In this technique, literally thousands of distinct oligonucleotide probes can be applied in an array on a silicon chip. A nucleic acid to be analyzed is fluorescently labeled and hybridized to the probes on the chip. It is also possible to study nucleic acid-protein interactions using these nucleic acid microchips. Using this technique one can determine the presence of mutations, sequence the nucleic acid being analyzed, or measure expression levels of a gene of interest. The method is one of parallel processing of many, even thousands, of probes at once and can tremendously increase the rate of analysis.

Alteration of mRNA transcription can be detected by any techniques known to persons of ordinary skill in the art.

These include Northern blot analysis, PCR amplification and RNase protection. Diminished mRNA transcription indicates an alteration of the wild-type gene.

Polymorphisms in the ACP1 gene also can be detected by screening for alteration of ACP1 protein. For example, monoclonal antibodies immunoreactive with the ACP1*A allele can be used to screen a tissue. Lack of cognate antigen would indicate absence of the ACP1*A allele. Antibodies specific for products of the ACP1*A mutant allele also could be used to detect the product of this allele. Such immunological assays can be done in any convenient format known in the art. These include Western blots, immunohistochemical assays and ELISA assays. Any means for detecting an altered protein can be used to detect polymorphisms of the ACP1 gene. Functional assays, such as protein binding determinations, also can be used. In addition, assays which detect biochemical function can be used.

The diagnostic method of the present invention is useful to clinicians for aiding decisions as to an appropriate course (s) of treatment. It is also contemplated by the present invention that determination of heterozygosity versus homozygosity will further aid in diagnosis of Alzheimer's disease.

Primer pairs specific for the ACP1 gene or the ACP1*A allele are useful for determination of the nucleotide sequence of a particular ACP1 allele using PCR. The pairs of single-stranded DNA primers can be annealed to sequences within or surrounding the ACP1 gene in order to prime amplifying DNA synthesis of the gene itself. Allele-specific primers also can be used. Such primers anneal only to particular ACP1 alleles, and thus will only amplify a product in the presence of the particular allele as a template. In one embodiment, the allele-specific primers will amplify a nucleic acid comprising the ACP1*A allele but not other allelic variants.

In order to facilitate subsequent cloning of amplified sequences, primers may have restriction enzyme site sequences appended to their 5' ends. Thus, all nucleotides of the primers are derived from ACP1 sequences or sequences adjacent to ACP1, except for the few nucleotides necessary to form a restriction enzyme site. Such enzymes and sites are well known to persons of ordinary skill in the art. The primers themselves can be synthesized using techniques which are well known to persons of ordinary skill in the art. Generally, the primers can be made using oligonucleotide synthesizing machines which are commercially available.

The nucleic acid probes provided by the present invention are useful for a number of purposes. They can be used in Southern hybridization to genomic DNA and in the RNase protection method for detecting point mutations. The probes can be used to detect PCR amplification products. They may also be used to detect mismatches with the ACP1 gene or mRNA using other techniques.

In order to detect a ACP1 gene variant, a biological sample is prepared and analyzed for a difference between the sequence of the allele being analyzed and the sequence of other known alleles. In a preferred embodiment, the allele detected is the ACP1*A allele.

"Antibodies." The present invention also provides polyclonal and/or monoclonal antibodies and fragments thereof, and immunologic binding equivalents thereof, which are capable of specifically binding to the ACP1*A polypeptide and fragments thereof or to polynucleotide sequences from the ACP1*A region, particularly from the ACP1 locus or a portion thereof. The term "antibody" is used both to refer to a homogeneous molecular entity, or a mixture such as a serum product made up of a plurality of different molecular entities. Antibodies will be useful in assays as well as pharmaceuticals. Antibodies to the ACP1*A will particularly be useful in detecting the allele and aiding in the diagnosis of a predisposition to Alzheimer's disease, especially early onset AD.

An immunological response is usually assayed with an immunoassay. Normally, such immunoassays involve some purification of a source of antigen, for example, that produced by the same cells and in the same fashion as the antigen. A variety of immunoassay methods are well known by persons of ordinary skill in the art.

As used herein, the singular form "a", "an", and "the" include plural references unless the context clearly indicates otherwise.

As used herein, the terms "diagnosing" or "prognosing," as used in the context of Alzheimer's disease, are used to indicate classification, severity or monitoring of the disease progression, prior to, during or after treatment. Signs and symptoms associated with Alzheimer's disease are well known by those skilled in the art and include for example neurofibrillary tangles; Alzheimer's plaques; memory loss; and decreased ability to learn or perform a task. Various models for detecting learning and memory impairments and other tests such as for example water maze tests and passive avoidance tasks are well known by those skilled in the art and can be utilized in animal models of the present invention.

Polynucleotide compositions useful in the practice of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. The polynucleotides of the invention may be isolated or substantially pure.

cDNA or genomic libraries of various types may be screened as natural sources of the nucleic acids of the ACP1*A allele, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

"Probes". Polynucleotide polymorphisms associated with ACP1 alleles, including alleles which predispose to Alzheimer's disease, can be detected by hybridization with a polynucleotide probe which forms a stable hybrid with that of the target sequence, under highly stringent to moderately stringent hybridization and wash conditions. If it is expected that the probes will be perfectly complementary to the target sequence, high stringency conditions will be used. Hybridization stringency may be lessened if some mismatching is expected, for example, if variants are expected with the result that the probe will not be completely complementary. Conditions are chosen which rule out nonspecific/adventitious bindings, that is, which minimize noise.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid, and can be determined by techniques well known by persons of ordinary skill in the art.

Probes for alleles may be derived from the sequences of the region or its cDNAs. The probes may be of any suitable length, which span all or a portion of the region, and which allow specific hybridization to the region.

The probes will include an isolated polynucleotide attached to a label or reporter molecule and may be used to isolate other polynucleotide sequences having sequence similarity, by standard methods. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change ligand-binding affinities, interchain affinities, or the polypeptide degradation or turnover rate.

A polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

Homologous polypeptides may be fusions between two or more polypeptide sequences or between the sequences of the ACP1*A allele and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding and may include for example partners such as immunoglobulins, bacterial β-galactosidase, trpE, protein A, β-lactamase, alpha amylase, alcohol dehydrogenase and yeast alpha mating factor.

Fusion proteins will typically be made by either recombinant nucleic acid methods, as described below, or may be chemically synthesized. Techniques for the synthesis of polypeptides are well known by persons of ordinary skill in the art.

"Protein purification" refers to various methods for the isolation of polypeptides from other biological material, such as from cells transformed with recombinant nucleic acids encoding ACP1, and are well known by persons of ordinary skill in the art. For example, such polypeptides may be purified by immunoaffinity chromatography employing, e.g., the antibodies provided by the present invention. Various methods of protein purification are well known by persons of ordinary skill in the art.

Polypeptides comprising the ACP1*A allele, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques.

Large amounts of the polynucleotides may be produced by a suitable host cell transformed with a nucleotide sequence encoding the ACP1*A ACP1 protein. Natural or synthetic polynucleotide fragments coding for the peptide or a desired fragment can be incorporated into recombinant polynucleotide constructs (vectors), usually DNA constructs, capable of introduction into and replication in a prokaryotic or eukaryotic cell. Usually the vectors will be suitable for replication in a unicellular host, such as yeast or bacteria, but may also be intended for introduction to (with and without integration within the genome) cultured mammalian or plant or other eukaryotic cell lines. The most commonly used prokaryotic hosts are strains of *Escherichia coli*, although other prokaryotes, such as *Bacillus subtilis* or *Pseudomonas* may also be used. Mammalian or other eukaryotic host cells, such as those of yeast, filamentous fungi, plant, insect, or amphibian or avian species, may also be useful for production of the proteins of the present invention.

Prokaryotic or eukaryotic cells transformed with the polynucleotides of the present invention are useful not only for the production of the nucleic acids and polypeptides of the present invention, but also, for example, in studying the characteristics of ACP1 polypeptides.

Antisense polynucleotide sequences are useful in preventing or diminishing the expression of the ACP1*allele, as will be appreciated by those skilled in the art. For example, polynucleotide vectors containing all or a portion of the locus or other sequences from the region (particularly those flanking the locus) may be placed under the control of a promoter in an antisense orientation and introduced into a cell. Expression of such an antisense construct within a cell will interfere with transcription and/or translation and/or replication.

In order to detect the presence of a ACP1 allele predisposing an individual to Alzheimer's disease, a biological sample such as blood is prepared and analyzed for the presence or absence of predisposing alleles of ACP1. Such diagnoses may be performed by diagnostic laboratories, or, alternatively, diagnostic kits are manufactured and sold to health care providers or to private individuals for self-diagnosis.

Initially, the screening method may involve amplification of the relevant ACP1 sequences. In another preferred embodiment of the invention, the screening method involves a non-PCR based strategy. Such screening methods can include for example two-step label amplification methodologies that are well known to persons of ordinary skill in the art. Both PCR and non-PCR based screening strategies can detect target sequences with a high level of sensitivity. As will readily be appreciated by those skilled in the art, the ACP1*A allele can be detected with various techniques, including for example PCR and enzymatic digestion of the TaqI site, PCR amplification with specific primers (i.e., allele-specific amplification) and or hybridization analysis of genomic DNA with a probe that specifically hybridizes to one ACP1 allele which can be the ACP1*A allele or another allele (i.e., allele specific probes as oligonucleotides).

Preferred embodiments relating to methods for detecting ACP1 polymorphisms include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies.

This invention is particularly useful for screening compounds by using a non-ACP1*A ACP1 polypeptide or ACP1 ACP1*A polypeptide or a binding fragment of said polypeptides in any of a variety of drug screening techniques.

The polypeptide or fragment employed in such a test may either be free in solution, affixed to a solid support, or borne on a cell surface. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between an ACP1 polypeptide or fragment and the agent being tested, or examine the degree to which the formation of a complex between a ACP1 polypeptide and a substrate, e.g., tau, APP, insulin receptor or platelet derived growth factor, is interfered with by the agent being tested.

The present invention extends, in various aspects, not only to a substance identified using a nucleic acid molecule as a modulator of polypeptide activity, in accordance with what is disclosed herein, but also to a pharmaceutical composition, medicament, drug or other composition comprising such a substance, methods comprising administration of such a composition comprising such a substance, methods comprising administration of such a composition to a patient, e.g., for treatment of Alzheimer's disease, use of such a substance in the manufacture of a composition for administration, e.g., for treatment of Alzheimer's disease, and a method of making a pharmaceutical composition comprising admixing such a substance with a pharmaceutically acceptable excipient, vehicle or carrier, and optionally other ingredients.

The present invention contemplates an antisense polynucleotide that hybridizes with mRNA molecules that encode an ACP1 ACP1*A polypeptide, and the use of one or more of those polynucleotides in treating Alzheimer's disease. An antisense polynucleotide can for example be administered by gene therapy. The polynucleotide may be introduced into the cell in a vector such that the polynucleotide remains extrachromosomal. In such a situation, the polynucleotide will be expressed by the cell from the extrachromosomal location. Vectors for introduction of polynucleotides for extrachromosomal maintenance are known in the art, and any suitable vector may be used. The antisense polynucleotide, may be employed in gene therapy methods in order to decrease the amount of the expression products of mutant ACP1 in Alzheimer's disease.

According to the present invention, a method is also provided of supplying ACP1 function to a cell that carries the ACP1 ACP1*A allele. The ACP1 gene or a part of the gene, may be introduced into the cell in a vector such that the gene remains extrachromosomal. In such a situation, the gene will be expressed by the cell from the extrachromosomal location. More preferred is the situation where the wild-type gene or a part thereof is introduced into the mutant cell in such a way that it recombines with the endogenous mutant ACP1 gene present in the cell. Such recombination requires a double recombination event, which results in the correction of the gene mutation. Vectors for introduction of genes both for recombination and for extrachromosomal maintenance are known in the art, and any suitable vector may be used. Methods for introducing DNA into cells such as electroporation, calcium phosphate coprecipitation and viral transduction are known in the art, and the choice of method is within the competence of the person of ordinary skill in the art.

Cells and animals which carry an ACP1*A ACP1 allele can be used as model systems to study and test for substances which have potential as therapeutic agents. The cells are typically cultured cells and may be isolated from individuals or experimental animals having the allele. The cell line can be engineered to carry the allele. Animals for testing therapeutic agents can be selected after mutagenesis of whole animals or after treatment of germline cells or zygotes. Such treatments include insertion of polymorphic ACP1 alleles, usually from a second animal species, as well as insertion of disrupted homologous genes. Alternatively, the endogenous ACP1 gene(s) of the animals may be disrupted using conventional techniques to produce knockout or transplacement animals. A transplacement is similar to a knockout because the endogenous gene is replaced, but in the case of a transplacement the replacement is by another version of the same gene. After test substances have been administered to the animals, the animals are assessed for expression of symptoms associated with Alzheimer's disease, including neurofibrillary tangles; Alzheimer's plaques; memory loss; and decreased ability to learn or perform a task. These animal models provide an extremely important testing vehicle for potential therapeutic products.

The practice of the present invention employs, unless otherwise indicated, conventional techniques of chemistry, molecular biology, microbiology, recombinant DNA, genetics, immunology, cell biology, cell culture and transgenic biology, which are within the skill of the art.

The present invention is described by reference to the following Examples, which are offered by way of illustration and are not intended to limit the invention in any manner. Standard techniques well known by persons of ordinary skill in the art and/or the techniques specifically described below were utilized.

EXAMPLE 1

Alzheimer's disease Subjects: All subjects examined in this study were non-Hispanic Caucasians. DNA was isolated from 142 brain samples, comprised of 42 Early Onset Alzheimer's Disease (EOAD) and 100 Late Onset Alzheimer's Disease (LOAD) patients, with a postmortem confirmed diagnosis of Alzheimer's disease from the Human Neurological Research Specimen Bank at Los Angeles Veterans Affairs Medical Center, Los Angeles, Calif. All cases were sporadic Alzheimer's disease. Patients were grouped according to age at onset. Those with an age of onset of 64 years of age or less were termed Early Onset Alzheimer's Disease or EOAD. Those with an age of onset of 65 years of age or greater were termed Late Onset Alzheimer's Disease or LOAD. These age distinctions were based on studies of others (Terry and Davies 1980; Terry and Katzman 1983; Kehoe et al.1999). The distribution of the age at death for the EOAD cases had a range of 55–78 years, with a mean age of 65.7 years (S.D. 5.4). The age at onset of EOAD cases ranged between 49 and 64 years, with a mean onset age of 58.5 years. There were 28 male and 14 female EOAD cases. The distribution of the age at death for the LOAD cases ranged from 67–97 years, with a mean age of 80.7 years (S.D. 6.6). The age at onset of the LOAD cases ranged from 65–94 years, with a mean onset age of 75.3 years. There were 55 male and 46 female LOAD cases.

Control Subjects≧55 years of age: DNA was obtained from blood leukocytes for age matched control samples (n=181) which consisted of four cohorts: (1) 59 healthy senior veterans participating in an athletic event; (2) 22 adult patients from Loma Linda University; (3) 44 adult patients from a local Veterans hospital; and (4) DNA extracted from 56 brain samples of elderly deceased subjects. There were 99 males and 77 females. The patients in the latter two groups had non-dementing medical conditions. The age range of those control subjects was 56–92, with a mean of 65.25 (S.D. 6.8) years.

Control Subjects<55 years of age: DNA was obtained from blood leukocytes for control samples (n=643) which consisted of two cohorts: (1) students from the University of California at San Bernardino Calif., (2) parents of twins in the Minnesota Family and Twin Study (Iacono et al., 1999). In both groups subjects with psychiatric disease or substance abuse were excluded. These subjects ranged in age from 21 to 54 years of age. Both control groups were non-Hispanic Caucasians. The study was approved by the Institutional Review Board and all controls signed an informed consent. DNA was isolated from brain samples or blood using standard techniques.

Genotyping: DNA was isolated from brain samples or blood using standard techniques. Genotyping of the ACP1*A Taq I (A>216G; CAA>CGA; Gln>105Arg) polymorphism was performed utilizing the following primers: Primer P1 is a 21 mer having the sequence as set forth in SEQ ID NO:1 (5'-TTCAGAAGACCCTAGCAGATG-3'). Primer P2 is a 26 mer having the sequence as set forth in SEQ ID NO:2 (5'-ACATAATAGGGATCTTCGATAATAAG-3'). Genomic DNA was isolated using techniques well known in the art. PCR conditions were as follows: 95° C. for 5 minutes; 35 cycles of 95° C. for 30 seconds, 54° C. for 1 minute and 72° C. for 1 minute; after 35 cycles samples were incubated for 5 minutes at 72° C. and then stored at 4° C. until restriction enzyme digestion and gel electrophoresis. Following amplification, samples were digested with TaqI restriction enzyme and the digested samples were analyzed by electrophoresis through 10% acrylamide gels at 180 volts. Using these methods, the ACP1*A allele generates a 110 base pair fragment while a non-ACP1*A allele generates a 190 base pair fragment. The TaqI restriction enzyme site characteristic of the ACP1*A allele has been described previously and is characterized as a CAA>CGA substitution at codon 105, which creates a Gln>Arg substitution at this codon (Sensabaugh et al. 1993)). Other suitable primers based on the known sequences of the genes are also used to amplify genomic DNA. The amplified products are digested with TaqI as described.

Statistics: The frequencies of the alleles and genotypes were compared by Chi square analysis. The trend for the genotype frequencies progressing from the controls≧55 years of age, to the LOAD, to the EOAD cases was assessed by the Mantel-Haenszel chi square test for linear association. To assess the percent of the variance of the LOAD and EOAD cases accounted for by the ACP1 gene, a genotype score was used in which individuals with a 11 genotype were scored a 0, those with a 12 genotype as 1, and those with a 22 genotype as 2. As noted infra, numerical genotypes indicate the following allelic compositions: genotype 11=absence of *A variant; genotype 12=50% *A variant; genotype 22=100% *A variant. For an Alzheimer's disease score the controls≧55 years of age were scored as 0 and those with EOAD were scored as 1. This Alzheimer's disease score was used as the dependent variable and the genotype score was used as the independent variable in a logistic regression analysis. All four subjects groups were tested to determine if they were in Hardy-Weinberg equilibrium. The SPSS statistical package (SPSS, Inc, Chicago, Ill.) was used for all statistical analyses.

The frequencies of the ACP1 alleles and genotypes for the four groups of subjects, are shown in Table 1. The control group for ≧55 years was not in Hardy-Weinberg equilibrium (p<0.025). The remaining three groups were in equilibrium. For the controls<55 years of age the frequency of the 2 allele was 0.34. This decreased to 0.25 for the age matched controls≧55 years. It was 0.33 for the LOAD cases and 0.48 for EOAD cases. Compared to controls≧55 this was of modest significance for the LOAD cases (p≦0.03) and quite significant for the EOAD cases (p≦0.0005).

For both the controls<55 years of age and the controls≧55 years of age, 11 was most common genotype at 44.5 and 53.0% respectively. Also in both, the 12 heterozygotes were modestly less (43.1 and 44.8% respectively). The major difference was in the frequency of the 22 homozygotes which was 12.4% for the controls<55 years of age and 2.2% for those ≧55 years of age. For LOAD cases the 12 genotype was most common (46.65) and the frequency of the 22 homozygotes was higher (9.7%) than for the age matched controls (9.7%). This was different from controls at a modest level of significance (p=0.013). For EOAD cases heterozygotes were by far the most common (57.1%), versus 23.8% for the 11 homozygotes and 19% for the 22 homozygotes. This was different from controls≧55 years of age at a high level of significance (p≦0.000008). The controls≧55 differed from the total set of Alzheimer's disease subjects at p≦0.0016. By regression analysis, the ACP1 gene accounted for 4.5% of the variance of EOAD, 1.5% of all Alzheimer's disease, but only 0.7% of LOAD.

TABLE 1

The number and percent or frequency of the ACP1 genotypes and alleles for the four groups of subjects

|  |  | 11 | 12 | 22 | Total |  | 1 | 2 |
|---|---|---|---|---|---|---|---|---|
| Controls <55 yr | N | 286 | 277 | 80 | 577 | freq | .66 | .34 |
|  | % | 44.5 | 43.1 | 12.4 |  |  |  |  |
| Controls ≧55 yr | N | 96 | 81 | 4 | 181 | freq | .75 | .25 |
|  | % | 53.0 | 44.8 | 2.2 |  |  |  |  |
| LOAD | N | 45 | 48 | 10 | 103 | freq | .67 | .33 |
|  | % | 43.7 | 45.6 | 9.7 |  |  |  |  |
| EOAD | N | 10 | 24 | 8 | 42 | freq | .51 | .49 |
|  | % | 23.8 | 57.1 | 19.0 |  |  |  |  |

Statistics for Genotypes

Controls×LOAD×EOAD: $\chi^2$=23.90, d.f.=4, p$\leq$0.00008
Mantel-Haenszel linear $\chi^2$=23.90, d.f.=4, p$\leq$0.00001
Controls$\geq$55×all AD: $\chi^2$=17.49, d.f.=2, p$\leq$0.0016
Controls$\geq$55×EOAD:$\chi^2$=25.19, d.f.=2, p$\leq$0.000008
Controls$\geq$55×LOAD:$\chi^2$=8.69, d.f.=2, p$\leq$0.013

Statistics for Alleles

Controls$\geq$55×all AD$\chi^2$=12.23 d.f.=1, p$\leq$0.0005
Controls$\geq$55×LOAD$\chi^2$=4.66 d.f.=1, p$\leq$0.03
Controls$\geq$55×EOAD$\chi^2$=4.66 d.f.=1, p<0.0001

The control group$\geq$55 years was not in Hardy-Weinberg equilibrium (p<0.025). The remaining three groups were in equilibrium. For the controls<55 years of age the frequency of the 2 allele was 0.34. This decreased to 0.25 for the age matched controls$\geq$55 years. It was 0.33 for the LOAD cases and 0.49 for EOAD cases. Compared to controls$\geq$55 years this was of modest significance for the LOAD cases (p$\leq$0.03) and quite significant for the EOAD cases (p$\leq$0.0005).

For both the controls<55 years of age and the controls 55 years of age, 11 was most common genotype at 44.5 and 53.0% respectively. Also in both, the 12 heterozygotes were modestly less frequent (43.1 and 44.8% respectively). The major difference was in the frequency of the 22 homozygotes which was 12.4% for the controls<55 years of age and 2.2% for those $\geq$55 years of age. For LOAD cases the 12 genotype was most common (46.65) and the frequency of the 22 homozygotes was higher (9.7%) than for the age matched controls (2.2%). This was different from controls at a modest level of significance (p=0.013). For EOAD cases heterozygotes were by far the most common (57.1%), versus 23.8% for the 11 homozygotes and 19% for the 22 homozygotes. These genotype frequencies were different from controls$\geq$55 years of age at a high level of significance (p$\leq$0.000008). The controls$\geq$55 differed from the total set of AD subjects at p$\leq$0.0016.

EXAMPLE 2

A larger sampling of LOAD patients were analyzed for occurrence of the 2 allele as in Example 1. The results of the association of ACP1 with LOAD is shown in Table 2 (number and percent of subjects with each genotype for controls and LOAD subjects, the chi square and the p value). These data include the LOAD individuals from Example 1 expanded with additional individuals diagnosed with LOAD. These results demonstrate that the association of ACP1*A with Alzheimer's disease may be limited to EOAD.

TABLE 2

| Genotype | Controls | LOAD |
|---|---|---|
| 11 | 150 (50.7%) | 95 (46.62%) |
| 12 | 121 (40.9%) | 89 (43.6%) |
| 22 | 25 (8.4%) | 20 (9.8%) |

$\chi^2$ = 0.880
p = 0.644

Discussion

Analysis of the ACP1 gene in older obese individuals has indicated that the ACP1*A allele is also associated with increased triglyceride levels. This suggests that the ACP1 gene is a longevity gene and that in a healthy control group the frequency of the ACP1*A allele might decrease with age, due to the earlier death of those carrying this allele. To test this the frequency of the ACP1*A allele in healthy individuals of several age groups including the <55 and $\geq$55 controls was determined. The decreased frequency in the $\geq$55 year old controls was significant, p$\leq$0.0014. Without being bound by theory, this is likely the reason the genotypes in this group were slightly out of Hardy-Weinberg equilibrium. Based on these findings, age-matched controls were considered important in order to determine if the ACP1 gene was associated with Alzheimer's disease. Thus, all Alzheimer's disease comparisons were with the controls$\geq$age 55. This showed a progressive increase in the frequency of the ACP1*A allele of the AC1 gene, from 0.25 for controls$\geq$55 years, to 0.33 for LOAD cases, to 0.49 for EOAD cases. These differences were modestly significant (p$\leq$0.03) for the LOAD cases, and more significant for the EOAD cases.

Figure 1:
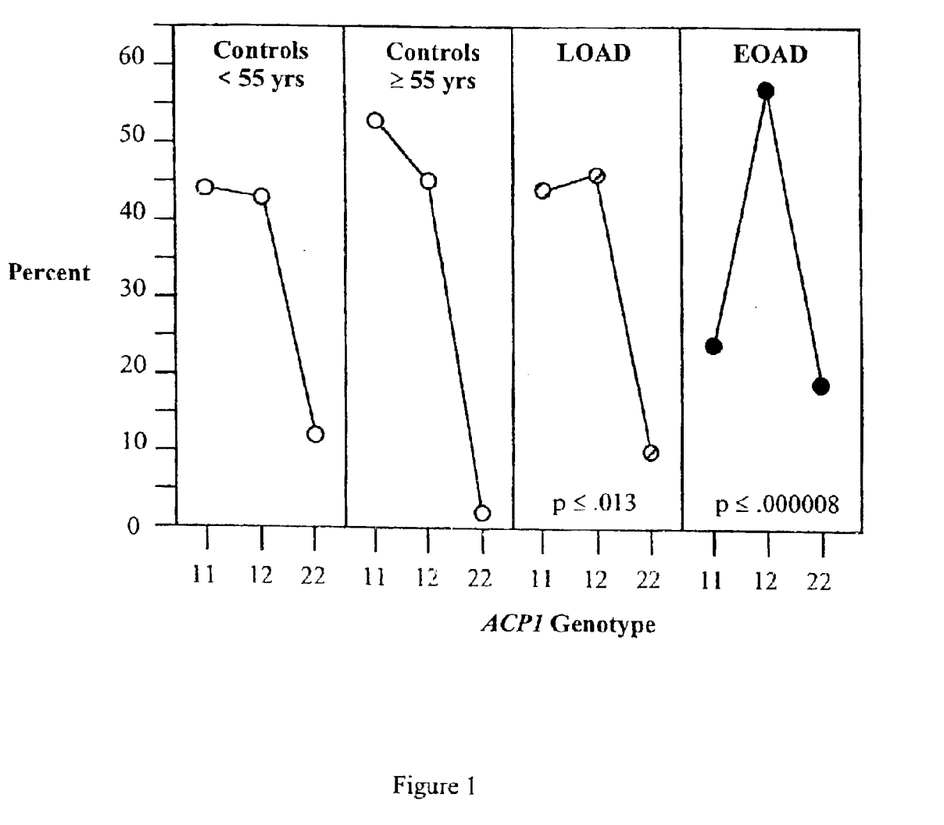
FIG. 1. Diagram of the genotype frequencies of the ACP1 gene in two control groups, and one set of data from LOAD and EOAD subjects.

The genotype distributions are also shown in figure form in FIG. 1. The 11 genotype was the most common genotype in controls$\geq$55 years while the 12 genotype was most common in both LOAD and EOAD cases. This was much more dramatic for the EOAD cases where the frequency of the 22 genotype began to approach that of the 11 genotype. The differences in the frequency of both the alleles and the genotypes between controls$\geq$55 years and EOAD cases indicates there was a significant increase in the frequency of the less active 2 allele in EOAD. The results of the regression analysis indicated that the ACP1 gene accounted for 4.5% of the variance of EOAD. While this may seem small, with other polygenic disorders each gene accounts for less than 2% of the variance in most cases (Comings et al. 2000(a); Comings et al. 2000 (b); Comings et al. 2000(c)).

The present study showed a significant increase in the frequency of the ACP1*A allele in EOAD.

Okadaic acid, through an inhibition of phosphatases and a stimulation of can account for both of the hallmarks of Alzheimer's disease, NFT and senile Since sporadic Alzheimer's disease is a polygenic disorder, the okadaic results paralleled by the additive and epistatic interaction of genetic variants of one or kinases, leading to an increase in their activity, and of genetic variants or one or phosphatases, leading to a decrease in their activity. Genetic imbalance in phosphatase activity may provide one of the major pathways to Alzheimer's and is one of the few mechanisms that explains the presence of both NFT and plaques in Alzheimer's disease, as strengthened by our findings of the role of a variant of the ACP1 gene in EOAD.

Bibliography

Alzheimer's Disease Collaborative Group. The structure of the presenilin 1 (S182) gene and identification of six novel mutations in early onset AD families. *Nature Genet.* 1995; 11: 219–222.

Arai, H., Ishiguro, K., Ohno, H., Moriyama, M., Itoh, N., Okamura, N., Matsui, T., Morikawa, Y., Horikawa, E., Kohno, H., Sasaki, H., & Imahori, K. CSF phosphorylated tau protein and mild cognitive impairment: a prospective study. *Exp Neurol* 2000; 166: 201–3.

Arendt, T., Holzer, M., Fruth, R., Bruckner, M. K., & Gartner, U. Paired helical filament-like phosphorylation of tau, deposition of beta/A4-amyloid and memory impairment in rat induced by chronic inhibition of phosphatase 1 and 2A. *Neuroscience,* 1995; 69:(3), 691–8.

Bennecib, M., Gong, C. X., Grundke-Iqbal, I., & Iqbal, K. Inhibition of PP-2A upregulates CaMKII in rat forebrain and induces hyperphosphorylation of tau at Ser 262/356. *FEBS Lett* 2001; 490: 15–22.

Braak, H., & Braak, E. Evolution of the neuropathology of Alzheimer's disease. *Acta Neurol. Scand.* 1996; 165 (Suppl): 3–12.

Bryson, G. L., Massa, H., Trask, B. J., & Van Etten, R. L. Gene structure, sequence, and chromosomal localization of the human red cell-type low-molecular-weight acid phosphotyrosyl phosphatase gene, ACP1. *Genomics* 1995; 30: 133–40.

Bucciantini, M., Chiarugi, P., Cirri, P., Taddei, L., Stefani, M., Raugei, G., Nordlund, P., & Ramponi, G. The low Mr phosphotyrosine protein phosphatase behaves differently when phosphorylated at Tyr131 or Tyr132 by Src kinase. *FEBS Lett,* 1999; 456:(1), 73–8.

Chernoff, J., & Li, H. C. A major phosphotyrosyl-protein phosphatase from bovine heart is associated with a low-molecular-weight acid phosphatase. *Arch Biochem Biophys,* 1985; 240:(1), 135–45.

Cirri, P., Chiarugi, P., Taddei, L., Raugei, G., Camici, G., Manao, G., & Ramponi, G. Low molecular weight protein-tyrosine phosphatase tyrosine phosphorylation by c-Src during platelet-derived growth factor-induced mitogenesis correlates with its subcellular targeting. *J Biol Chem,* 1998; 273:(49), 32522–7.

Comings D E, Gade-Andavolu R, Gonzalez N, Wu S, Muhleman D, Blake H et al. Comparison of the role of dopamine, serotonin, and noradrenergic genes in ADHD, ODD and conduct disorder. Multivariate regression analysis of 20 genes. Clinical Genetics 2000a;57:178–96.

Comings D D, Gade-Andavolu R, Gonzalez N, Wu S, Muhleman D, Blake H et al. Multivariate Analysis of Associations of 42 Genes in ADHD, ODD and Conduct Disorder. Clinical Genetics 2000b;58:31–40.

Comings D E, Gade-Andavolu R, Gonzalez N, Wu S, Muhleman D, Blake H et al. A Multivariate Analysis of 59 Candidate Genes in Personality Traits:The Temperament Character Inventory. Clinical Genetics 2000c;58:375–85.

Daly N L, Hoffmann R, Otvos L, Craik D J. Role of phosphorylation in the conformation of tau peptides implicated in Alzheimer's disease. Biochemistry 2000;39:9039–46.

Dissing, J., & Johnsen, A. H. Human red cell acid phosphatase (ACP1): the primary structure of the two pairs of isozymes encoded by the ACP1*A and ACP1*C alleles. *Biochim Biophys Acta* 1992; 1121:(3), 261–8.

Flaherty, D. B., Soria, J. P., Tomasiewicz, H. G., & Wood, J. G. Phosphorylation of human tau protein by microtubule-associated kinases: GSK3beta and cdk5 are key participants. *J Neurosci Res* 2000; 62: 463–72.

Grant, W. B. Dietary links to Alzheimer's disease. *Alzheimer's Disease Review* 1997; 2: 42–55.

Guise, S., Braguer, D., Carles, G., Delacourte, A., & Briand, C. Hyperphosphorylation of tau is mediated by ERK activation during anticancer drug-induced apoptosis in neuroblastoma cells. *J Neurosci Res* 2001; 63: 257–67.

Holzer, M., Bruckner, M. K., Beck, M., Bigl, V., & Arendt, T. Modulation of APP processing and secretion by okadaic acid in primary guinea pig neurons. *J Neural Transm,* 2000; 107:(4), 451–61.

Hopkinson, D. A., Spencer, N., & Harris, H. *The Principles of Human Biochemical Genetics* (3rd ed.).1980. Amsterdam: Elsevier.

Iacono, W. G., Carlson, S. R., Taylor, J., Elkins, I. J., McGue, M. Behavioral disinhibition and the development of substance-use disorders: Findings from the Minnesota Twin Family Study. *Development and Psychopathology* 1999; 11:869–900.

Iijima, K., Ando, K., Takeda, S., Satoh, Y., Seki, T., Itohara, S., Greengard, P., Kirino, Y., Nairn, A. C., & Suzuki, T. Neuron-specific phosphorylation of Alzheimer's beta-amyloid precursor protein by cyclin-dependent kinase 5. *J Neurochem,* 2000; 75:(3), 1085–91.

Ikura, Y., Kudo, T., Tanaka, T., Tanii, H., Grundke-Iqbal, I., & Takeda, M. Levels of tau phosphorylation at different sites in Alzheimer's disease brain. *NeuroReport* 1998; 9: 2375–2379.

Iqbal, K., Alonso, A. C., Gong, C. X., Khatoon, S., Pei, J. J., Wang, J. Z., & Grundke-Iqbal, I. Mechanisms of neurofibrillary degeneration and the formation of neurofibrillary tangles. *J Neural Transm Suppl* 1998; 53:(18), 169–80.

Iqbal, K., Grundke-Iqbal, I., & Zaidi, T. Defective brain microtubule assembly in Alzheimer's disease. *Lancet* 1986; 2: 421–426.

Karlinsky, H., Vaula, G., Haines, J. L., Ridgley, J., Bergeron, C., Mortilla, M., Tupler, R., Percy, M., Robitaille, Y., Crapper, M., & St.George-Hyslop, P. Molecular and prospective phenotypic characterization of a pedigree with Familial Alzheimer's disease and a missence mutation in codon 717 of the b-amyloid precursor protein (APP) gene. *Neurology* 1992; 42: 1445–1453.

Kawai, M., Cras, P., Richey, P., Tabaton, M., Lowery, D. E., Gonzalez-DeWhitt, P. A., Greenberg, B. D., Gambetti, P., & Perry, G. Subcellular localization of amyloid precursor protein in senile plaques of Alzheimer's disease. *Am J Pathol* 1992; 140: 947–58.

Kehoe, P., Wavrant-De Vrieze, F., Crook, R., Wu, W. S., Holmans, P., Fenton, I., Spurlock, G., Norton, N., Williams, H., Williams, N., Lovestone, S., Perez-Tur, J., Hutton, M., Chartier-Harlin, M. C., Shears, S., Roehl, K., Booth, J., Van Voorst, W., Ramic, D., Williams, J., Goate, A., Hardy, J., & Owen, M. J. A full genome scan for late onset Alzheimer's disease. *Hum Mol Genet* 1999; 8:(2), 237–45.

Kerokoski, P., Suuronen, T., Salminen, A., Soininen, H., & Pirttila, T. The levels of cdk5 and p35 proteins and tau phosphorylation are reduced during neuronal apoptosis. *Biochem Biophys Res Commun,* 2001; 280: 998–1002.

Kimura, T., Yamamoto, H., Takamatsu, J., Yuzuriha, T., Miyamoto, E., & Miyakawa, T. Phosphorylation of MARCKS in Alzheimer disease brains. *Neuroreport,* 2000; 11:(4), 869–73.

Lazaruk, K. D., Dissing, J., & Sensabaugh, G. F. Exon structure at the human ACP1 locus supports alternative splicing model for f and s isozyme generation. *Biochem Biophys Res Commun* 1993; 196: 440–6.

Lee, G., Newman, S. T., Gard, D. L., Band, H., & Panchamoorthy, G. Tau interacts with src-family non-receptor tyrosine kinases. *J Cell Sci,* 1998; 111:( Pt 21), 3167–77.

Lovestone, S., & Reynolds, C. H. The phosphorylation of Tau: a critical stage in neurodevelopment and neurodegenerative process. *Neuroscience* 1997; 78: 309–324.

Lovestone, S., Reynolds, C. H., Latimer, D., Davis, D. R., Anderton, B. H., Gallo, J. M., & et/al. Alzheimer's disease-like phosphorylation of the microtubule-associated protein tau by glycogen synthase kinase-3 in translocated mammalian cells. *J. Curr. Biol.* 1994; 4: 1077–1086.

McLaughlin, M., & Breen, K. C. Protein kinase C activation potentiates the rapid secretion of the amyloid precursor protein from rat cortical synaptosomes. *J Neurochem,* 1999; 72:(1), 273–81.

Mailliot, C., Sergeant, N., Bussiere, T., Caillet-Boudin, M. L., Delacourte, A., & Buee, L. Phosphorylation of specific sets of tau isoform reflects different neurofibrillary degeneration processes. *FEBS Lett.* 1998; 433: 101–104.

Masliah, E., Cole, G., Shimohama, S., Hansen, L., DeTeresa, R., Terry, R. D., & Saitoh, T. Differential involvement of protein kinase C isozymes in Alzheimer's disease. *J Neurosci,* 1990; 10:(7), 2113–24.

Masliah, E., Mallory, M., Hansen, L., Alford, M., Albright, T., Terry, R., Shapiro, P., Sundsmo, M., & Saitoh, T.

Immunoreactivity of CD45, a protein phosphotyrosine phosphatase, in Alzheimer's disease. *Acta Neuropathol (Berl),* 1991; 83:(1), 12–20.

Morris, J. C., Storandt, M., Miller, J. P., McKeel, D. W., Price, J. L., Rubin, E. H., & Berg, L. Mild cognitive impairment represents early-stage Alzheimer disease. *Arch Neurol,* 2001; 58:(3), 397–405.

National Institute on Aging/Alzheimer's Association Working Group. Apolipoprotein E genotyping in Alzhemier's disease. *Lancet* 1996; 347: 1091–1095.

Omar, R., Pappolla, M., Argani, I., & Davis, K. Acid phosphatase activity in senile plaques and cerebrospinal fluid of patients with Alzheimer's disease. *Arch Pathol Lab Med* 1993; 117: 166–9.

Oawal_Dewan, M., Sen, P. C., Abdel Ghany, M., Shalloway, D., & Racker, E. Phsophorylation of tau protein by purified p34cdc28 and a related protein kinase from neurofilaments. *J. Biol. Chem.* 1992; 267: 19705–19709.

Ono, T., Yamamoto, H., Tashima, K., Nakashima, H., Okumura, E., Yamada, K., Hisanaga, S.-L., Kishimoto, T., Miyakawa, T., & Miyamoto, E. Dephosphorylation of abnromal sites of tau factor by protein phosphatases and its implication for Alzheimer's disease. *Neurochem. Int.* 1995; 26: 205–215.

Pei, J. J., Grundke-Iqbal, I., Iqbal, K., Bogdanovic, N., Winblad, B., & Cowbum, R. F. Accumulation of cyclin-dependent kinase 5 (cdk5) in neurons with early stages of Alzheimer's disease neurofibrillary degeneration. *Brain Res,* 1998; 797:(2), 267–77.

Penninger, J. M., Irie-Sasaki, J., Sasaki, T., & Oliveira-Dos-Santos, A. J. CD45: new jobs for an old acquaintance. *Nat Immunol,* 2001; 2:(5), 389–96.

Russ, C., Lovestone, S., & Powell, J. F. Identification of sequence variants and analysis of the role of glycogen synthase kinase 3 b gene and promoter in late onset Alzheimer's disease. *Mol.Psychiary* 2001; 6: 320–324.

St George-Hyslop, P. H., Tanzi, R. E., Polinsky, R. J., Haines, J. L., Nee, L., Watkins, P. C., Myers, R. H., Feldman, R. G., Pollen, D., Drachman, D., & et al. The genetic defect causing familial Alzheimer's disease maps on chromosome 21. *Science* 1987; 235: 885–890.

Schellenberg, G. D., Bird, T. D., Wijsman, E. M., Orr, H. T., Anderson, L., Nemens, E., White, J. A., Bonnycastle, L., Weber, J. L., Alonso, M. E., Potter, H., Heson, L. L., & Martin, G. M. Genetic linkage evidence for a familial Alzheimer's disease locus on chromosome 14. *Science* 1992; 258: 668–671.

Selkoe, D. J. Toward a comprehensive theory for Alzheimer's disease. Hypothesis: Alzheimer's disease is casued by the cerebral accumulation and cytotoxicity of amyoid b-protein. *Ann. N.Y. Academy Sciences* 2000; 924: 17–25.

Sensabaugh, G. F., & Lazaruk, K. A. A TaqI site identifies the *A allele at the ACP1 locus. *Hum Mol Genet* 1993; 2: 1079.

Shapiro, I. P., Masliah, E., & Saitoh, T. Altered protein tyrosine phosphorylation in Alzheimer's disease. *J Neurochem.* 1991; 56: 1154–1162.

Shimohama, S., Fujimoto, S., Chachin, M., Taniguchi, T., Perry, G., Whitehouse, P. J., & Kimura, J. Alterations of low molecular weight acid phosphatase protein level in Alzheimer's disease. *Brain Res* 1995; 699: 125–9.

Shimohama, S., Fujimoto, S., Taniguchi, T., Kameyama, M., & Kimura, J. Reduction of low-molecular-weight acid phosphatase activity in Alzheimer brains. *Ann Neurol* 1993; 33: 616–21.

Shirazi, S. K. and Wood, J. G. The protein tyrosine kinase, fyn, in Alzheimer's disease pathology. Neuroreport 1993 4(4), 435–7.93.

Sobue, K., Agarwal-Mawal, A., Li, W., Sun, W., Miura, Y., & Paudel, H. K. Interaction of neuronal Cdc2-like protein kinase with microtubule-associated protein tau. *J Biol Chem* 2000; 275: 16673–80.

Sontag, E., Nunbhakdi-Craig, V., Lee, G., Brandt, R., Kamibayashi, C., Kuret, J., White, C. L., Mumby, M. C., & Bloom, G. S. Molecular interactions among protein phosphatase 2A, tau, and microtubules. Implications for the regulation of tau phosphorylation and the development of tauopathies. *J Biol Chem* 1999; 274: 25490–8.

Sontag, E., Nunbhakdi-Craig, V., Lee, G., Bloom, G. S., & Mumby, M. C. Regulation of the phosphorylation state and microtubule-binding activity of Tau by protein phosphatase 2A. *Neuron,* 1996; 17:(6), 1201–7.

Spencer, N., Hopkinson, D. A., & Harris, H. Quantitative differences and gene dosage in the human red cell acid phosphatase polymorphism. *Nature* 1964; 201: 299–300.

Sperber, B. R., Leight, S., Goedert, M., & Lee/V. M. Glycogen synthase kinase-3b phosphorylates tau protein at multiple sites in intact cells. *Neuroscience Letters* 1995; 197: 149–153.

Standen, C. L., Brownlees, J., Grierson, A. J., Kesavapany, S., Lau, K. F., McLoughlin, D. M., & Miller, C. C. Phosphorylation of thr(668) in the cytoplasmic domain of the Alzheimer's disease amyloid precursor protein by stress-activated protein kinase 1b (Jun N-terminal kinase-3). *J Neurochem,* 2001; 76:(1), 316–20.

Su, J. H., Cummings, B. J., & Cotman, C. W. Early phosphorylation of tau in Alzheimer's disease occurs at Ser-202 and is preferentially located within neurites. *NeuroReport* 1994; 5: 2358–2362.

Taddei, M. L., Chiarugi, P., Cirri, P., Talini, D., Camici, G., Manao, G., Raugei, G., & Ramponi, G. LMW-PTP exerts a differential regulation on PDGF- and insulin-mediated signaling. *Biochem Biophys Res Commun,* 2000; 270:(2), 564–9.

Tan, S., Maher, P., & Schubert, D. The role of protein phosphorylation in beta amyloid toxicity. *Brain Res* 1997; 765: 159–63.

Taniguchi, T., Kawamata, T., Mukai, H., Hasegawa, H., Isagawa, T., Yasuda, M., Hashimoto, T., Terashima, A., Nakai, M., Ono, Y., & Tanaka, C. Phosphorylation of tau is regulated by pkn. *J Biol Chem,* 2001; 276:(13), 10025–31.

Tanino, H., Yoshida, J., Yamamoto, R., Kobayashi, Y., Shimohama, S., & Fujimoto, S. Abundance of low molecular weight phosphotyrosine protein phosphatase in the nerve-ending fraction in the brain. *Biol Pharm Bull* 1999; 22: 794–8.

Terry, R. D., & Davies, P. Dementia of the Alzheimer's type. *Ann. Rev.Neurosci.* 1980; 3: 77–95.

Terry, R. D., & Katzman, R. Senile dementia of the Alzheimer's type. *Ann. Neurol.* 1983; 14: 497–506.

Terry, R. D., Masliah, E., & Hansen, L. A. Structural basis of the causative alterations in Alzheimer's disease. R. D. Terry, R. Katzman, & K. L. Bick *Alzheimer's Disease* (1994). New York: Raven Press.

Tseng, H. C., Lu, Q., Henderson, E., & Graves, D. J. Phosphorylated tau can promote tubulin assembly. *Proc Natl Acad Sci U S A* 1999; 96:(17), 9503–8.

Vogelsberg-Ragaglia, V., Schuck, T., Trojanowski, J. Q., & Lee, V. M. PP2A mRNA Expression Is Quantitatively Decreased in Alzheimer's Disease Hippocampus. *Exp Neurol* 2001; 168: 402–12.

Walter, J., Schindzielorz, A., Hartung, B., & Haass, C. Phosphorylation of the beta-amyloid precursor protein at the cell surface by ectocasein kinases 1 and 2. *J Biol Chem,* 2000; 275,(31), 23523–9.

Zhang, Z. Y., & Van Etten, R. L. Purification and characterization of a low-molecular-weight acid phosphatase—a phosphotyrosyl-protein phosphatase from bovine heart. *Arch Biochem Biophys,* 1990; 282:(1), 39–49.

What is claimed is:

1. A method to determine whether a person is at increased risk for developing Alzheimer's disease, the method comprising determining the ACP1 genotype of said person, wherein the presence of the ACP1*A allele indicates an increased risk of said person for developing Alzheimer's disease.

2. The method of claim 1 wherein said Alzheimer's disease is early onset Alzheimer's disease.

3. A method as in claim 1 wherein said determination comprises contacting a sample of said person's nucleic acid with a probe or primer specific for the ACP1*A allele.

* * * * *